(12) United States Patent
Hubner et al.

(10) Patent No.: US 6,186,422 B1
(45) Date of Patent: Feb. 13, 2001

(54) NOZZLE ASSEMBLY FOR AIR ABRASION SYSTEM

(75) Inventors: Henry Hubner, Amityville; Eddy Paultre, West Hempstead, both of NY (US)

(73) Assignee: Air Techniques, Hicksville, NY (US)

( * ) Notice: Under 35 U.S.C. 154(b), the term of this patent shall be extended for 0 days.

(21) Appl. No.: 09/378,943

(22) Filed: Aug. 23, 1999

Related U.S. Application Data

(60) Provisional application No. 60/102,503, filed on Sep. 30, 1998.

(51) Int. Cl.$^7$ ..................................................... B05B 1/00
(52) U.S. Cl. .................................. 239/589; 239/DIG. 19; 433/88; 451/90; 451/102
(58) Field of Search ............................... 239/589, DIG. 8, 239/DIG. 19; 433/88; 451/90, 102

(56) References Cited

U.S. PATENT DOCUMENTS

| | | | |
|---|---|---|---|
| 1,940,972 | * 12/1933 | Schwartzkoff | 239/589 X |
| 2,641,839 | * 6/1953 | Black | 533/88 X |
| 4,236,889 | * 12/1980 | Wright | 433/88 X |
| 5,094,402 | * 3/1992 | Perret, Jr. et al. | 239/DIG. 19 |
| 5,123,840 | * 6/1992 | Nates | 433/95 |
| 5,127,831 | * 7/1992 | Bab | 433/88 X |
| 6,024,566 | * 2/2000 | Bruns et al. | 433/88 X |

* cited by examiner

*Primary Examiner*—Andres Kashnikow
*Assistant Examiner*—Robin O. Evans
(74) *Attorney, Agent, or Firm*—Clifford G. Frayne

(57) ABSTRACT

A nozzle assembly for a hand piece in an air abrasion system for delivering an abrasive laden air stream to a surface, the nozzle assembly having a connecting member having a channel and being removably mountable to said hand piece, an arcuate conduit member having a channel, the conduit member secured to the connecting member and a nozzle member formed with the channel, the nozzle member mounted within the channel of the conduit member, the nozzle member defined by a tapered channel portion in fluid communication with the channel of the conduit member and a cylindrically-shaped channel portion in communication with said tapered channel portion for directing the abrasive laden air stream in a substantially cylindrically-shaped cross section to the surface to be abraded.

13 Claims, 1 Drawing Sheet

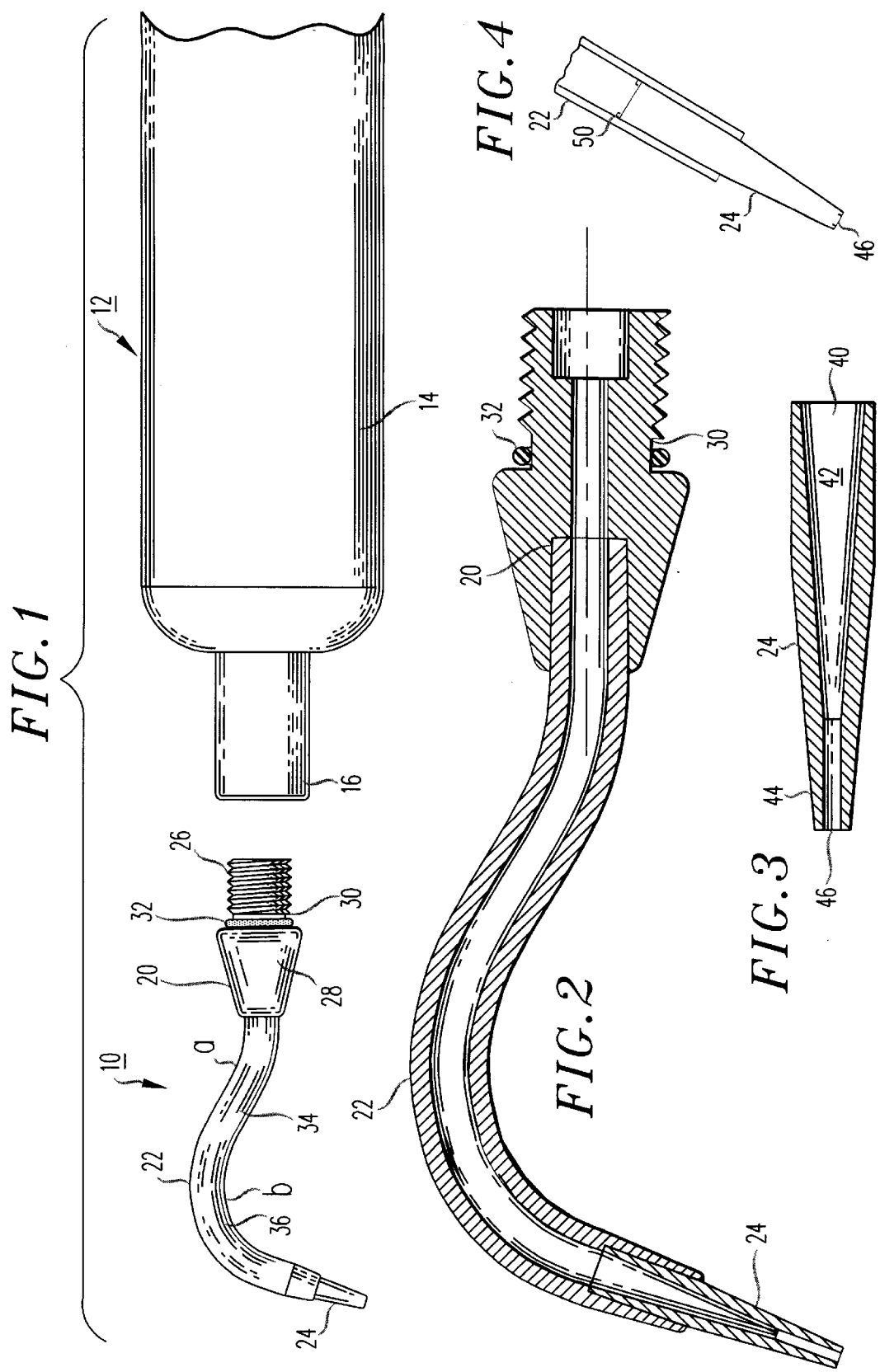

NOZZLE ASSEMBLY FOR AIR ABRASION SYSTEM

RELATED APPLICATIONS

This application is based on provisional U.S. application Ser. No. 60/102,503, filed Sep. 30, 1998 and claims the benefit of such filing date.

BACKGROUND OF THE INVENTION

1. Field of Invention

The present invention relates to an air abrasion system and in particular to a dental air abrasion system for removing and/or cutting tooth structure, amalgam, composites, or other tooth filling materials and/or stain, and more particularly relates to a nozzle assembly for such an abrasive system. However, the air abrasion system has other medical uses such as in the field of dermatology.

2. Description of the Prior Art

Air abrasion systems have been used in dentistry for cutting tooth structure, such as enamel and dentin. The systems typically comprise a source of compressed fluid, preferably air, a source of abrasive particulate matter, for example, aluminum oxide particulate, a chamber for mixing or suspending the desired quantity of abrasive particulate matter in a fluid air stream, a valve for adjusting the pressure of the fluid air stream, and a delivery system for such particulate laden stream to the tooth structure being treated.

Typically, the abrasive particulate laden air stream is caused to impinge upon the tooth structure and thereby cut the tooth structure, amalgam, composite or dental tooth filling depending upon the particular dental procedure. Dental abrasive air systems have been known for many years, but are now gaining more acceptability as a result of technological innovations.

One of the reasons for the failure of dental air abrasion systems to gain widespread acceptability was the inability to direct the abrasive particulate laden air stream accurately on the tooth structure, amalgam, composite or dental tooth filling. The abrasive particulate laden air stream once exiting the nozzle had a tendency to fan out or expand in cross-sectional area and not only prevented a directed abrasive particulate laden air stream on the point of the tooth structure requiring the dental procedure, but also interfered with the dentist's ability to observe the abrading characteristics of the particulate laden air stream to insure that only that portion of the tooth structure requiring the abrasion is actually being abraded.

Air abrasion also has other applications in the medical field and in particular, in the field of dermatology and Applicant's novel contribution as detailed hereafter would also have application in this field because of the benefits obtained by Applicant's nozzle assembly.

OBJECTIONS OF THE INVENTION

An object of the present invention is to provide for a nozzle assembly for an air abrasion system which provides a more focused abrasive particulate laden air stream.

Another object of the present invention is to provide for a nozzle assembly for an air abrasion system which minimizes visual impairment and permits the operator to more accurately observe the abrading process.

A still further object of the present invention is to provide for a nozzle assembly for a dental air abrasion system which removes and/or cuts tooth structure, amalgam, composites, or other dental tooth filling materials with reduced amounts of abrasive particulate matter.

SUMMARY OF THE INVENTION

There is disclosed a nozzle assembly for a hand piece for an abrasion system having a connector member including a channel removably mounted to the dental hand piece, a conduit member having a channel and including an arcuate position and secured to the connecting member and a nozzle member formed with a channel defined by a tapered portion extending towards a cylindrically-shaped portion having an exit opening.

BRIEF DESCRIPTION OF THE DRAWINGS

These and other objects of the present invention will become evident particularly when taken in light of the following illustrations wherein:

FIG. 1 is a partial exploded view of a hand piece with the novel assembly; and

FIG. 2 is a side cross-sectional view of the nozzle assembly; and

FIG. 3 is a side cross-sectional view of the nozzle member; and

FIG. 4 is a partial enlarged view of the nozzle member in cooperation with the conduit member.

DETAILED DESCRIPTION OF THE DRAWINGS

The present invention as described hereafter has application air abrasion systems generally and in particular to air abrasion systems utilized in the dental and medical fields. In the medical field, one such area would be that of dermatology. However, for purposes of illustration, the detailed description of the apparatus will be described in reference to dental procedures.

Referring now to the drawings, and particularly FIGS. 1 and 2, there is illustrated a nozzle assembly, generally indicated as 10, for a dental hand piece, generally indicated as 12, to be held by a dentist or dental technician for effecting dental air abrasion processes. The dental hand piece 12 is comprised of a body member 14 (partially shown) having a coupling portion 16 for cooperating with the nozzle assembly 10, as more fully hereinafter disclosed. The dental hand piece 12 is connected by conduit (not shown) with a source of pressurized fluid, such as air and a reservoir of abrasive particulate matter, such as aluminum oxide. The dental hand piece 12 may also contain a controlling mechanism for initiating and terminating the flow of pressurized air abrasive particulate matter.

The nozzle assembly 10 of the present invention is comprised of a connecting member 20, a conduit member 22 and a nozzle member 24. The connector member 20 is formed with an externally threaded fastener portion 26 for cooperating with internal threads (not shown) of the coupling portion 16 of the dental hand piece 12. The connector member includes a collar portion 28 including an annular recess 30 between the collar portion 28 and the threaded portion 26 for positioning an O-ring 32 to insure proper seating and prevent bypass leaking upon securing the connecting member 20 of the nozzle assembly 10 to the dental hand piece 12 as more fully hereinafter disclosed.

The conduit member 22 is comprised of a tubular body 34 including an arcuate-shape portion 36 and is secured within the connecting member 20, preferably utilizing an interference fit. Preferably, the conduit member 22 is between 1 inch and 1½ inches in length. The arcuate-shape portion 36 of the conduit member is of an arc such that axis of nozzle member 24 forms an angle with the axis of connecting member 20 of between 10 degrees to 105 degrees, and permits the dentist or dental technician to facilely manipulate the nozzle assembly 12 within the oral cavity of the patient to reach teeth of both the upper and lower jaw. With respect to the arcuate bend in conduit member 22, as illustrated, the radius of the first curvature a immediately after conduit member 22 connecting member 20 is 0.312 inches. The radius of the second curvature of conduit member 22 as it bends downwardly at b is 0.219 inches. The conduit member 22 is formed of a stainless steel type of material, e.g. type 302, 303, 304 or 316 which is capable of repeated aseptic procedures.

The nozzle member 24, referring particularly to FIGS. 3 and 4, mounted within the conduit member 22 and is formed with a channel 40 including a tapered portion 42 and a cylindrically-shaped portion 44 of substantially constant cross-sectional area including an exit orifice 46. The tapered portion 42 is of diminishing diameter towards the cylindrically-shaped channel portion 44 of the channel 40 and this taper should be as gradual as possible. Cylindrically-shaped portion 44 of channel 40 preferably has a length in the range of between 5 and 10 times its diameter. Its diameter and that of exit orifice 46 are in the range of between 0.014 and 0.018 inches.

The nozzle member 24 is formed of a carbide-type material such as tungsten carbide—cobalt alloys, capable of withstanding the abrasive action of the abrasive laden air stream as well as repeated aseptic procedures.

Nozzle member 24 is slidably receivable within conduit member 22. The manner in which it is secured is best illustrated in FIG. 4 which is a partial cross-section of conduit member 22 with nozzle member 24 inserted therein. There is formed on the inner circumference of conduit member 22, an annular shoulder 50. The inner diameter of conduit member 22 conforms to the outer diameter of nozzle member 24. Nozzle member 24 is slidably inserted into conduit member 22 until contact is made with shoulder 50. This insert distance is sufficient such that a portion of conduit member 22 extends over the tapered portion of nozzle member 24. Conduit member 22 is then crimped utilizing a swage process to make intimate contact with the outer circumference of nozzle member 24 at its tapered portion and thus secure nozzle member 24 to conduit member 22. Annular shoulder 50 extends inwardly from the inner circumference of conduit member 22, a distance equal to the thickness of the sidewall of nozzle member 24.

The nozzle assembly constructed in accordance with the recitations herein has been found to provide for an abrasive particulate laden air stream which maintains its cross sectional area when expelled from the nozzle and does not fan out or expand in cross sectional area such that the dentist can observe the tooth structure upon which the abrasive process is being performed and better control the abrasive process itself since the abrasive laden air stream is more focused. This advantage also has application in the medical field, particularly in dermatology where air abrasion is utilized in a variety of skin procedures.

While the invention has been described with respect to the exemplary embodiments thereof, it will be recognized by those of ordinary skill in the art that many additions or modifications can be made without departing from the scope of the invention and therefore it is manifestly intended that the invention be limited only by the claims and the equivalence thereof.

What is claimed is:

1. A nozzle assembly for a hand piece in an air abrasion system for delivering an abrasive laden air stream to a surface to be abraded which comprises:

a connecting member having a channel and removably mountable to said hand piece;

an arcuate conduit member having a channel in communication with said channel of said connecting member, said arcuate conduit member secured to said connecting member, said arcuate conduit member having an arcuate portion having an arc of from between 10 to 105 degrees;

a nozzle member formed with a delivery channel, said nozzle member mounted within said channel of said arcuate conduit member, said delivery channel of said nozzle member defined by a tapered channel portion in communication with said channel of said arcuate conduit member and a cylindrically-shaped channel discharge portion for directing said abrasive-laden air stream in substantially cylindrically-shaped in cross-section to said surface to be abraded.

2. The nozzle assembly in accordance with claim 1 wherein said conduit member is secured to said connecting member by a collar member by means of an interference fit.

3. The nozzle assembly in accordance with claim 1 wherein said conduit member has a maximum outer diameter of 0.15 inches and a minimum inner diameter of 0.050 inches.

4. The nozzle assembly in accordance with claim 1 wherein said arcuate portion of said conduit member is defined by a first radius of 0.312 inches and a second radius of 0.219 inches.

5. The nozzle assembly in accordance with claim 1 wherein said arcuate portion of said conduit member positions the axis of said nozzle member at an angle from the horizontal of between 10 and 105 degrees.

6. The nozzle assembly in accordance with claim 1 wherein the length of said cylindrically-shaped portion of said channel of said nozzle member is between 5 and 10 times its diameter.

7. The nozzle assembly in accordance with claim 1 wherein said cylindrically-shaped channel portion of said channel of said nozzle member has a diameter in the range of 0.014 to 0.018 inches.

8. The nozzle assembly in accordance with claim 1 wherein the said nozzle member is secured within the said conduit member by means of a swage fit.

9. The nozzle assembly in accordance with claim 1 wherein said nozzle member abuts an annular shoulder within said conduit member for mounting said nozzle member in said conduit member.

10. The nozzle assembly in accordance with claim 1 wherein said nozzle assembly is utilized to abrade tooth surfaces.

11. The nozzle assembly in accordance with claim 1 wherein said nozzle assembly is utilized to abrade skin surfaces.

12. The nozzle assembly in accordance with claim 1 wherein said nozzle assembly is fabricated from an abrasive resistant material.

13. The nozzle assembly as defined in claim 12 wherein said abrasive resistant material is a tungsten carbide cobalt material.

* * * * *